(12) United States Patent
Lau et al.

(10) Patent No.: US 8,303,983 B2
(45) Date of Patent: Nov. 6, 2012

(54) TARGETED LIPOSOMAL DRUG DELIVERY SYSTEM

(75) Inventors: John R. Lau, Howard, OH (US); W. Blair Geho, Wooster, OH (US); George H. Snedeker, Wooster, OH (US)

(73) Assignee: SDG, Inc., Cleveland, OH (US)

( * ) Notice: Subject to any disclaimer, the term of this patent is extended or adjusted under 35 U.S.C. 154(b) by 88 days.

(21) Appl. No.: 12/687,843

(22) Filed: Jan. 14, 2010

(65) Prior Publication Data

US 2010/0209492 A1 Aug. 19, 2010

Related U.S. Application Data

(60) Continuation of application No. 11/643,397, filed on Dec. 21, 2006, now abandoned, which is a division of application No. 09/313,828, filed on May 18, 1999, now Pat. No. 7,169,140.

(60) Provisional application No. 60/085,969, filed on May 19, 1998.

(51) Int. Cl.
*A61K 9/127* (2006.01)

(52) U.S. Cl. .................................. 424/450; 424/400

(58) Field of Classification Search .................. None
See application file for complete search history.

(56) References Cited

U.S. PATENT DOCUMENTS

| | | | |
|---|---|---|---|
| 3,150,160 A | 9/1964 | Dexter |
| 3,373,177 A | 3/1968 | Young |
| 3,710,795 A | 1/1973 | Higuchi et al. |
| RE28,819 E | 5/1976 | Thompson |
| 4,016,290 A | 4/1977 | Rahman |
| 4,141,911 A | 2/1979 | Matsumoto et al. |
| 4,224,179 A | 9/1980 | Schneider |
| 4,310,506 A | 1/1982 | Baldeschwieler et al. |
| 4,328,245 A | 5/1982 | Yu et al. |
| 4,358,603 A | 11/1982 | Yu |
| 4,409,239 A | 10/1983 | Yu |
| 4,410,545 A | 10/1983 | Yu et al. |
| 4,603,044 A | 7/1986 | Geho et al. |
| 4,714,607 A | 12/1987 | Klaveness |
| 4,744,989 A | 5/1988 | Payne et al. |
| 4,761,287 A | 8/1988 | Geho |
| 4,797,285 A | 1/1989 | Barenholz et al. |
| 4,863,896 A | 9/1989 | Geho et al. |
| 4,866,040 A | 9/1989 | Stracher et al. |
| 4,891,208 A | 1/1990 | Janoff et al. |
| 4,921,644 A | 5/1990 | Lau et al. |
| 4,942,036 A | 7/1990 | Geho et al. |
| 4,946,787 A | 8/1990 | Eppstein et al. |
| 5,000,960 A | 3/1991 | Wallach |
| 5,010,073 A | 4/1991 | Kappus et al. |
| 5,021,200 A | 6/1991 | Vanlerberghe et al. |
| 5,026,558 A | 6/1991 | Hwang |
| 5,104,661 A | 4/1992 | Lau |
| 5,128,121 A | 7/1992 | Berg et al. |
| 5,274,082 A | 12/1993 | Seri et al. |
| 5,288,499 A | 2/1994 | Janoff |
| 5,330,742 A | 7/1994 | Deutsch et al. |
| 5,382,421 A | 1/1995 | White et al. |
| 5,387,410 A | 2/1995 | Bosworth et al. |
| 5,407,660 A | 4/1995 | Bosworth et al. |
| 5,435,989 A | 7/1995 | Presant et al. |
| 5,466,467 A | 11/1995 | Singh |
| 5,512,294 A | 4/1996 | Li et al. |
| 5,534,241 A | 7/1996 | Torchilin et al. |
| 5,762,910 A | 6/1998 | Unger et al. |

FOREIGN PATENT DOCUMENTS

| | | |
|---|---|---|
| EP | 0071564 B1 | 7/1981 |
| EP | 0165728 A1 | 12/1985 |
| WO | WO 88/00474 | 1/1988 |

OTHER PUBLICATIONS

Burns, H.D., et al., *J. Pharm Sci*, "Improved Synthesis of N-(2,6-Dimethylphenylcarbomoylmethyl)imminodiacetic Acid and Analogs", vol. 67, No. 10, 1434-36 (Oct 1978).

Gaizer, F., et al., *Polyhedron*, "Protonation and Complex Formation Equilibria of N-(Phenylcarbamoylmethyl)iminodiacetic Acid Derivatives . . . ", vol. 11, No. 2, 257-64 (1992).

*Chemical Abstracts*, vol. 108, 306, 108:201341J (JP62-221660), Publication Year 1987.

*Primary Examiner* — Michael G Hartley
*Assistant Examiner* — Robert Cabral
(74) *Attorney, Agent, or Firm* — Riverside Law LLP

(57) ABSTRACT

A metal targeting complex which associates with a charged liposomal structure is provided. The metal targeting complex provides the targetability of the liposomal construct to the desired receptor sites of a warm-blooded host for therapy or diagnostic use.

6 Claims, 8 Drawing Sheets

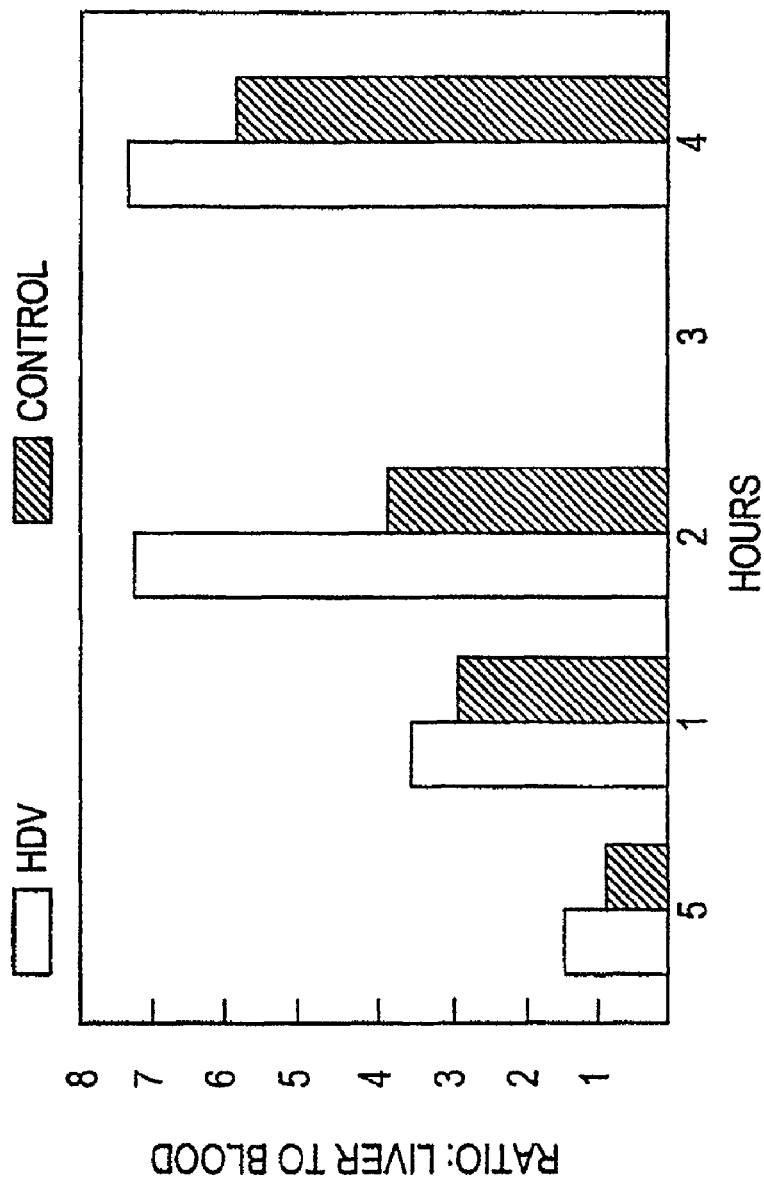
FIG. 8 - A GRAPH DEPICTING THE DISTRIBUTION OF HDV AND CONTROL LIPOSOMES OVER TIME IN THE MOUSE EXPRESSED AS A RATIO OF THE LIPOSOMES FOUND IN THE LIVER TO THOSE FOUND IN THE BLOOD

TARGETED LIPOSOMAL DRUG DELIVERY SYSTEM

CROSS-REFERENCE TO RELATED APPLICATIONS

This application is a continuation of U.S. patent application Ser. No. 11/643,397, filed Dec. 21, 2006, which is a divisional of U.S. patent application Ser. No. 09/313,828, filed May 18, 1999, which is entitled to priority under 35 U.S.C. §119(e), to U.S. Provisional Application No. 60/085,969, filed on May 19, 1998, each of which is herein incorporated by reference in its entirety.

FIELD OF THE INVENTION

This invention pertains to metal complexes, such as water insoluble chromium complexes, and to targeted liposomal drug delivery systems containing the complexes, particularly those useful for the delivery of an agent to the hepatocytes of the liver.

BACKGROUND OF THE INVENTION

Liposomes, also known as vesicles, are generally composed of phospholipids and other lipid components such as cholesterol. They can function as carriers whose essential structural feature is a bipolar lipid membrane which envelops an aqueous core volume in which pharmacological agents are solubilized and therefore encapsulated. Liposomal encapsulated drugs have shown promise in treating diseases and have performed as diagnostic tools for the early detection of cancer and other maladies. As a result, liposomes have shown potential as site-specific carrier systems for a variety of therapeutic agents including enzymes for enzyme replacement therapy, hormones, cell modifying agents and genetic material. The pharmaceutical products which have been delivered to designated sites in vivo have demonstrated an improvement in therapeutic indices. Thus, by using liposomes for site-specific delivery, the results show a general lowering of adverse side effects as lower overall doses of therapeutic agents are administered. Agents that are delivered in a conventional or non-specific manner often spread or are dispersed to non-designated areas and thus exhibit adverse side effects and unwanted pharmacological responses.

Various lipid formulations and methods for their preparation have been described for the delivery of pharmaceutically active agents to a host.

Geho and Lau in U.S. Pat. No. 4,603,044 describe a targeted liposomal delivery system for delivery of a drug to the hepatobiliary receptors of the liver. The system is composed of a drug or diagnostic agent encapsulated in or associated with lipid membrane structures in the form of vesicles or liposomes, and a molecule having a fatty substituent attached to the vesicle wall and a target substituent which is a biliary attracted chemical, such as a substituted iminodiacetate complex.

Geho in U.S. Pat. No. 4,761,287 describes the delivery of serotonin to the liver using a hepatocyte directed vesicle (HDV).

Geho and Lau in U.S. Pat. No. 4,863,896 disclose the delivery of encapsulated insulin in a hepatocyte directed vesicle in conjunction with a simultaneous supply of free insulin.

While there have been some advances in the art of targeted delivery systems, many of these systems have relied on the sequential addition of targeting moieties to the exterior surface of a liposomal membrane so that the carrier system can deliver the therapeutic to a designated site-of-action. The present invention is distinguishable from prior art systems in that particular target molecules, have been discovered that are not only hepatocyte specific, but can be incorporated into a liposomal carrier construct in a one-step addition procedure at the time of manufacture.

Accordingly, it is an object of this invention to provide a water-insoluble structure, e.g., a chromium complex, as well as other water-insoluble amorphous complexes, that will dissolve in a liposomal lipid matrix and enable the liposomal construct, in conjunction with a therapeutic or diagnostic cargo, to be delivered to the hepatocytes in the liver of a warm-blooded host.

Further, it is an object of the invention to provide an amorphous water insoluble target molecule in a dissociated form which is a product of the interaction between the essential target molecule and the liposomal membrane which produces a dissociated species that present itself as a hepatocyte targetable derivative of the parent compound.

It is also an object of the invention to produce a chemical means for synthesizing the amorphous organic target complex from aqueous media.

A still further object of the invention is to incorporate a hepatocyte targeting molecule into the liposomal construct utilizing a single-step manufacturing process.

An even further object of the invention is to produce an injectable form of the hormone insulin which is convenient to formulate either during the manufacturing process or later by a registered pharmacist thus making it easy for a diabetic patient to administer the insulin by subcutaneous injection.

Still another object of the invention is to provide a hepatocyte directed liposomal delivery system for insulin replacement therapy that will provide a means for achieving better glucose homeostasis in the liver and plasma of a warm-blooded host.

These and other objects and features of the invention will be apparent from the following summary and description of the invention and from the claims.

SUMMARY OF THE INVENTION

In accomplishing the foregoing and related objectives, the present invention is directed to a liposomal delivery system that utilizes a metal targeting complex, e.g., chromium or other metal complex, that is soluble in organic solvents, but substantially insoluble in aqueous media.

The particular diagnostic or therapeutic agent employed does not impose any significant limitation upon the scope of the invention. Any agent which is susceptible to liposomal entrapment or association, and the delivery of which may benefit from such association, is expected to be useful, e.g., antibiotics, antidepressants, antitumorigenics, antivirals, cytokines, hormones, imaging agents, neurotransmitters, stimulants, biogenic amines, diagnostics and the like.

BRIEF DESCRIPTION OF THE DRAWINGS

The following is a brief description of the drawings which are presented for the purposes of illustrating the invention and not for the purposes of limiting the same:

FIG. 8 depicts the distribution of HDV and control liposomes over time in a mouse model.

DETAILED DESCRIPTION OF THE INVENTION

Definitions

Figure 1:
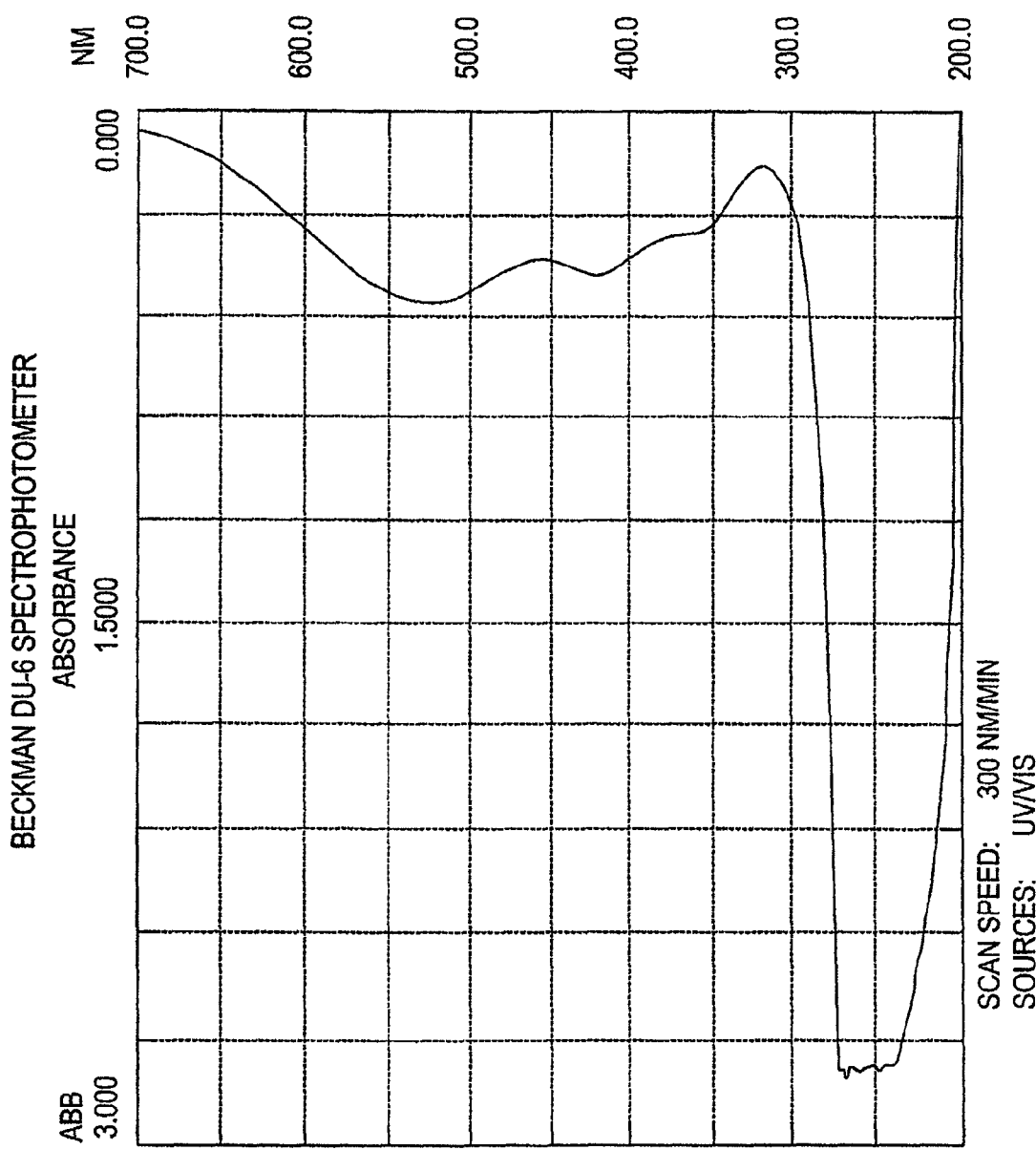
FIG. 1 illustrates the absorption spectrum of the chromium target complex.

As used herein, the term "lower" means the group it is describing contains from 1 to 6 carbon atoms;

the term "alkyl" refers to a straight or branched chain hydrocarbon containing no unsaturation, and one substitution site, e.g., methyl (—$CH_3$), ethyl (—$CH_2CH_3$), isopropyl [—$CH(CH_3)_2$], 2-butyl, neopental [$(CH_3)CCH_2$—], n-hexyl, etc.;

the term "alkylene" refers to a lower branched or unbranched alkyl group having two substitution sites, e.g., methylene (—$CH_2$—), ethylene (—$CH_2CH_2$—), isopropylene

etc.;

the term "aryl" refers to a cyclic carbon ring structure, with or without saturation, that has one substitution site which consists of a group, e.g., phenyl, m-methoxyphenyl, tolyl, sterol, etc., of the formula in Example #1 where Z is hydrogen, halogen, loweralkyl, loweralkoxy, $CF_3$, CN, $NO_2$, and $NH_2$ and p is an integer of 1 to 4;

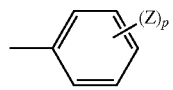

the term "arylloweralkyl" refers to an aryl group, as defined above, linked to a lower alkylene group, through one of the lower alkylene's substitution sites, leaving one site for further substitution on the lower alkylene group, and having the formula where Z and p are as previously defined;

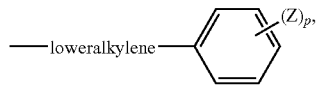

the term "alkoxy" refers to a substituent which contains an alkyl group and an ether oxygen having one site of substitution at the oxygen, e.g., methoxy (—$OCH_3$), ethoxy (—$OCH_2CH_3$), propoxy (—$OCH_2CH_2CH_3$), butoxy (—$OCH_2CH_2CH_2CH_3$), loweralkyl-O—;

pentoxy (—$OCH_2CH_2CH_2CH_2CH_3$), etc., and having the formula the term "acyl" refers to a substituent which contains an alkyl group linked to a carboxyl group having one site for substitution at the carboxyl carbon and having the formula shown

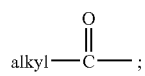

the term "halogen" refers to a member of the halogen family consisting of fluorine, chlorine, bromine, and iodine;

and the term "heterocyclic" refers to a substituent of a cyclic ring structure that contains one or more atoms besides carbon comprising the ring structure, e.g., pyrrole, imidazole, benzimidazole, phthalein, pyridenyl, pyranyl, (uranyl, thiophene, oxazole, pyrazole, 3-pyrroline, pyrrolidene, pyrimidine, purine, quinoline, isoquinoline, carbazole, etc.

The term "chromium target molecule complex" refers to a complex composed of a chromium (Cr) atom capable of accepting up to six ligands contributed by multivalent molecules, such as two molecules of N-(2,6-diisopropylphenyl-carbamoyl-methyl) iminodiacetic acid which is insoluble in water but soluble in organic solvents in contrast to prior art chromium complexes which are water soluble. Such an atom is referred to by its ligand association, as hexacoordinate or hexadentate.

The term "liposome" refers to a spherical lipid and phospholipid particle in which individual lipid molecules cooperatively interact to create a bipolar lipid membrane which encloses and isolates a portion of the medium in which it was formed.

Optionally, the liposomal construct is also provided with a masking agent in intimate association therewith to protect it from immunoreactive attack, such as by macrophages.

Applications

A suitable bridging agent or compound is selected. A suitable bridging agent is a selected metal compound, e.g., a salt of chromium, zirconium, vanadium, molybdenum, manganese, iron, yttrium, or niobium, etc., which is generally selected from the transition and inner transition metals or elements which can be divided into families. Also included are neighbors of the transition metals.

Furthermore, these transition metals or elements may be subdivided into two classes, depending upon whether the inside energy sublevel being filled is d or f. A series of elements in which electrons are being added more or less regularly to an inside d energy sublevel is spoken of simply as a "transition series." There are three complete transition series and a fourth which contains only actinium, Ac. A series of elements in which electrons are being added to an inside f energy sublevel is called an "inner transition series." There are two such inner transition series, the lanthanide and the actinide, which follow lanthanum and actinium, respectively, in the periodic table. The members of the transition series are shown in table form in TABLE I and following:

the scandium family: Sc (scandium), Y (yttrium), La (lanthanum) and the lanthanide series, Ac (actinium) and the actinide series;

the titanium family: Ti (titanium), Zr (zirconium), Hf (hafnium);

the vanadium family: V (vanadium), Nb (niobium), Ta (tantalum);

the chromium family: Cr (chromium), Mo (molybdenum), W (tungsten);

the manganese family: Mn (manganese), Tc (technetium), Re (rhenium);

the iron family: Fe (iron), Co (cobalt), Ni (nickel);

the platinum family: Ru (ruthenium), Rh (rhodium), Pd (palladium), Os (osmium), Ir (iridium), Pt (platinum).

The neighbors of the transition metals are:
the copper family: Cu (copper), Ag (silver), Au (gold);
the zinc family: Zn (zinc), Cd (cadmium), Hg (mercury);
the aluminum family: Al (aluminum), Ga (gallium), In (indium), Tl (thallium);
the germanium family: Ge (germanium), Sn (tin), Pb (lead);

Antimony (Sb) and bismuth (Bi), although metallic in character, are included in the nitrogen family and polonium (Po) is classified in the sulfur family.

| $1^{st}$ Series: | Sc Scandium | Ti Titanium | V Vanadium | Cr Chromium | Mn Manganese | Fe Iron | Co Cobalt | Ni Nickel |
|---|---|---|---|---|---|---|---|---|
| $2^{nd}$ Series: | Y Yttrium | Zr Zirconium | Nb Niobium | Mo Molybdenum | Tc Technetium | Ru Ruthenium | Rh Rhodium | Pd Palladium |
| $3^{rd}$ Series: | La Lanthanum | Hf Hafnium | Ta Tantalum | W Tungsten | Re Rhenium | Os Osmium | Ir Iridium | Pt Platinum |
| Lanthanide Series: | | Ce Cerium | Pr Praseodymium | Nd Neodymium | Pm Promethium | Sm Samarium | Eu Europium | Gd Gadolinium |
| | | Tb Terbium | Dy Dysprosium | Ho Holmium | Er Erbium | Tm Thulium | Yb Ytterbium | Lu Lutetium |
| $4^{th}$ Series: | Ac Actinium | | | | | | | |
| Actinide Series: | | Th Thorium | Pa Protactinium | U Uranium | Np Neptunium | Pu Plutonium | Am Americium | Cm Curium |
| | | Bk Berkelium | Cf Californium | Es Einsteinium | Fm Fermium | Md Mendelevium | No Nobelium | Lr Lawrenceium |

A suitable complexing agent or compound is selected. A suitable complexing agent is one which will complex with a selected metal bridging agent, e.g. a salt of chromium, zirconium, etc., to form a complex of such metal which is substantially insoluble in water and soluble in organic solvents.

By "substantially insoluble" is meant that the complex, such as the resultant chromium target molecule complex or other metal targeting complexes which may be crystalline or amorphous in composition that are formed with the complexing agents, exhibit the property of being insoluble in water at room temperature. Such a complex or a dissociated form thereof when associated with a liposomal lipid matrix forms a transport agent which functions to carry and deliver a therapeutic or diagnostic cargo, e.g., insulin, serotonin, antibiotics, diagnostics, imaging agents, etc., to a desired receptor site in a mammal, e.g., to hepatocytes in the liver of a warm-blooded host. By use of the term "associated with" is meant that the complex or its dissociated form is incorporated into or on the surface of or with the liposomal lipid matrix.

A first suitable complexing agent is selected from an iminodiacetic acid of the formula (1) where $R_1$ is loweralkyl, aryl, arylloweralkyl, and a heterocyclic substituent.

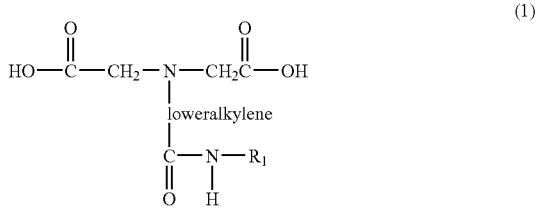

(1)

Some suitable compounds of the formula (1) include:
N-(2,6-diisopropylphenylcarbamoylmethyl)iminodiacetic acid;
N-(2,6-diethylphenylcarbamoylmethyl)iminodiacetic acid;
N-(2,6-dimethylphenylcarbamoylmethyl)iminodiacetic acid;
N-(4-isopropylphenylcarbamoylmethyl)iminodiacetic acid;
N-(4-butylphenylcarbamoylmethyl)iminodiacetic acid;
N-(2,3-dimethylphenylcarbamoylmethyl)iminodiacetic acid;
N-(2,4-dimethylphenylcarbamoylmethyl)iminodiacetic acid;
N-(2,5-dimethylphenylcarbamoylmethyl)iminodiacetic acid;
N-(3,4-dimethylphenylcarbamoylmethyl)iminodiacetic acid;
N-(3,5-dimethylphenylcarbamoylmethyl)iminodiacetic acid;
N-(3-butylphenylcarbamoylmethyl)iminodiacetic acid;
N-(2-butylphenylcarbamoylmethyl)iminodiacetic acid;
N-(4-tertiary butylphenylcarbamoylmethyl)iminodiacetic acid;
N-(3-butoxyphenylcarbamoylmethyl)iminodiacetic acid;
N-(2-hexyloxyphenylcarbamoylmethyl)iminodiacetic acid;
N-(4-hexyloxyphenylcarbamoylmethyl)iminodiacetic acid; aminopyrrol iminodiacetic acid;
N-(3-bromo-2,4,6-trimethylphenylcarbamoylmethyl)iminodiacetic acid; benzimidazole methyl iminodiacetic acid;
N-(3-cyano-4,5-dimethyl-2-pyrrylcarbamoylmethyl)iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl)iminodiacetic acid and other derivatives of N-(3-cyano-4-methyl-2-pyrrylcarbamoylmethyl)iminodiacetic acid of formula (2),

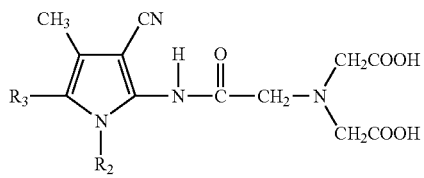

(2)

where $R_2$ and $R_3$ are the following,

| $R_2$ | $R_3$ |
|---|---|
| H | iso-$C_4H_9$ |
| H | $CH_2CH_2SCH_3$ |
| H | $CH_2C_6H_4$-p-OH |

| $R_2$ | $R_3$ |
|---|---|
| $CH_3$ | $CH_3$ |
| $CH_3$ | iso-$C_4H_9$ |
| $CH_3$ | $CH_2CH_2SCH_3$ |
| $CH_3$ | $C_6H_5$ |
| $CH_3$ | $CH_2C_6H_5$ |
| $CH_3$ | $CH_2C_6H_4$-p-$OCH_3$. |

A second suitable complexing agent is selected from an imino diacid derivative of the general formula (3), where $R_4$, $R_5$, and $R_6$ are independent of each other and can be hydrogen, lower alkyl, aryl, arylloweralkyl, alkoxyloweralkyl, and heterocyclic.

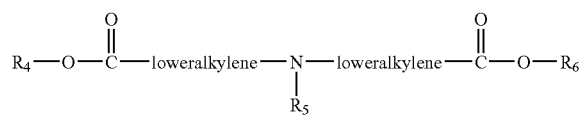

Some suitable compounds of the formula (3) include:
N'-(2-acetylnaphthyl)iminodiacetic acid (NAIDA);
N'-(2-naphthylmethyl)iminodiacetic acid (NMIDA);
iminodicarboxymethyl-2-naphthylketone phthalein complexone;
3β:7α:12α:trihydroxy-24-norchol anyl-23-iminodiacetic acid;
benzimidazole methyl iminodiacetic acid; and
N-(5,pregnene-3-β-ol-2-oyl carbamoylmethyl)iminodiacetic acid.

A third suitable complexing agent is selected from an amino acid of formula (4), where $R_7$ is an amino acid side chain, where $R_8$ is loweralkyl, aryl, arylloweralkyl, and where $R_9$ is pyridoxylidene, which is a Schiff Base derivative of pyridoxal phosphate. The Schiff derivative is shown in Formula (5).

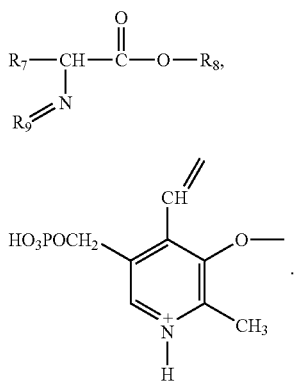

Some suitable amino acids of the formula (4) are aliphatic amino acids, including glycine, alanine, valine, leucine, isoleucine; hydroxyamino acids, including serine, and threonine; dicarboxylic amino acids and their amides, including aspartic acid, asparagine, glutamic acid, glutamine; amino acids having basic functions, including lysine, hydroxylysine, histidine, arginine; aromatic amino acids, including phenylalanine, tyrosine, tryptophan, thyroxine; sulfur-containing amino acids, including cysteine, methionine.

Other amino acids and derivatives of biological importance include, but are not necessarily limited to β-alanine, γ-amino butyric acid, O-diazoacetylserine (azaserine), homoserine, ornithine, citrulline, penicillamine.

Also included are examples of the members of the pyridoxylidene class including, but not limited to,
pyridoxylidene glutamate;
pyridoxylidene isoleucine;
pyridoxylidene phenylalanine;
pyridoxylidene tryptophan;
pyridoxylidene 5-methyl tryptophan;
pyridoxylidene-5-hydroxytryptamine; and
pyridoxylidene-5-butyltryptamine.

A fourth suitable complexing agent is selected from a diamine of the general formula (6), where $R_{10}$ is hydrogen, loweralkyl, aryl; $R_{11}$ is loweralkylene, arylloweralkyl; $R_{12}$ and $R_{13}$ independently are hydrogen, loweralkyl, alkyl, aryl, arylloweralkyl, acylheterocyclic, toluene, sulfonyl or tosulate,
Some suitable diamines of the formula (6) include,

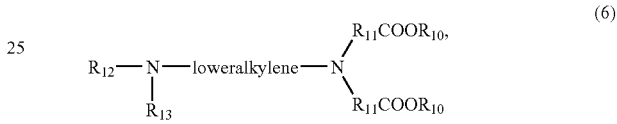

ethylene diamine-N,N diacetic acid;
ethylenediamine-N,N-bis(-2-hydroxy-5-bromophenyl)acetate;
N'-acetylethylene diamine-N,N diacetic acid;
N'-benzoyl ethylene diamine-N,N diacetic acid;
N'(p-toluenesulfonyl)ethylene diamine-N,N diacetic acid;
N'-(p-t-butylbenzoyl)ethylene diamine-N,N diacetic acid;
N'-(benzenesulfonyl)ethylene diamine-N,N diacetic acid;
N'-(p-chlorobenzenesulfonyl)ethylene diamine-N,N diacetic acid;
N'-(p-ethylbenzenesulfonyl ethylene diamine-N,N diacetic acid;
N'-acyl and N' sulfonyl ethylene diamine-N,N diacetic acid;
N'-(p-n-propylbenzenesulfonyl)ethylene diamine-N,N diacetic acid;
N'-(naphthalene-2-sulfonyl)ethylene diamine-N,N diacetic acid; and
N'-(2,5-dimethylbenzenesulfonyl)ethylene diamine-N,N diacetic acid.

Other suitable complexing compounds or agents include:
Penicillamine;
β-mercaptoisobutyric acid;
dihydrothioctic acid;
6-mercaptopurine;
kethoxal-bis(thiosemicarbazone);
Hepatobiliary Amine Complexes,
1-hydrazinophthalazine(hydralazine);
sulfonyl urea;
Hepatobiliary Amino Acid Schiff Base Complexes;
pyridoxylidene glutamate;
pyridoxylidene isoleucine;
pyridoxylidene phenylalanine;
pyridoxylidene tryptophan;
pyridoxylidene 5-methyl tryptophan;
pyridoxylidene-5-hydroxytryptamine;
pyridoxylidene-5-butyltryptamine;
tetracycline;
7-carboxy-β-hydroxyquinoline;

phenolphthalein;
eosin I bluish;
eosin I yellowish;
verograffin;
3-hydroxyl-4-formyl-pyridene glutamic acid; and
Azo substituted iminodiacetic acid.
Also included are the following,
hepatobiliary dye complexes, such as
rose bengal;
congo red;
bromosulfophthalein;
bromophenol blue;
toluidine blue; and
indocyanine green;
hepatobiliary contrast agents, such as
iodipamide; and
ioglycamic acid;
bile salts, such as bilirubin;
cholgycyliodohistamine; and
thyroxine;
hepatobiliary thio complexes, such as penicillamine;
β-mercaptoisobutyric acid;
dihydrothiocytic acid;
6-mercaptopurine; and
kethoxal-bis(thiosemicarbazone);
hepatobiliary amine complexes, such as
1-hydrazinophthalazine (hydralazine);
and sulfonyl urea;
hepatobiliary amino acid Schiff Base complexes, including
pyridoxylidene-5-hydroxytryptamine; and
pyridoxylidene-5-butyltryptamine;
hepatobiliary protein complexes, such as
protamine;
ferritin; and
asialo-orosomucoid;
and asialo complexes, such as
lactosaminated albumin;
immunoglobulins, G, IgG; and
hemoglobin.

A suitable metal compound that is the selected bridging agent intended to be complexed with the complexing agent, is one which is soluble in water and capable of forming a coordinated complex with the aforementioned hepatocyte directed molecules: Some suitable metal compounds of the designated bridging agents include compounds of chromium, e.g., chromium chloride (III), hexahydrate, chromium (III) fluoride tetrahydrate, chromium (III) bromide hexahydrate; compounds of zirconium, e.g., zirconium (IV) citrate ammonium complex, zirconium (IV) chloride, zirconium (IV) fluoride hydrate, zirconium (IV) iodide; compounds of molybdenum, e.g., molybdenum (III) bromide, molybdenum (III) chloride, molybdenum (IV) sulfide; compounds of iron, e.g., iron (III) hydrate, iron (III) phosphate tetrahydrate and iron (III) sulfate pentahydrate.

A selected complexing agent, e.g., an iminodiacid, such as N-(2,6-diisopropylphenylcarbamoylmethyl)iminodiacetic acid, is reacted with a selected metal compound, e.g., chromium chloride hexahydrate; zirconium (IV) citrate ammonium complex or a manganese or molybdenum compound, with metal in excess, in an amount sufficient to complex with an isolatable portion of the complexing agent. The reaction is conducted at a temperature of 20° C. to 33° C. for 24 to 96 hours, or until the resultant complex precipitates out of the aqueous buffered media, e.g., chromium chloride solution buffered by 10 mM sodium acetate buffer at a final pH of 3.2-3.3. The resultant precipitated complex is then destined to be incorporated into a suitable liposome matrix or liposomal membrane.

It is noted that after the destined initial incorporation of the resultant metal complex into, on or with a destined liposomal membrane, e.g. of distearoyl lecithin, cholesterol, dicetyl phosphate, a portion thereof is converted, after a time period from a few minutes to several days and at a temperature of 4° C. to 60° C., into a dissociated moiety or a combination thereof, such as the metal salts, e.g., 1,2-distearoyl-sn-glycero-3-phosphocholine-Cr or dicetyl phosphate-Cr or other salts. Alternatively, the in situ created generic constructs that may be produced by molecular rearrangement within the liposomal membrane are, for example, 1,2-distearoyl-sn-glycero-3-phosphocholine-Cr-dissociated target molecule component or dicetylphosphate-Cr-dissociated target molecule component or simply the dissociated target molecule with no metal present. When the metal is present, the metal moiety forms an ionic bridge between the phospholipid moiety and a molecule that has preference for the hepatobiliary receptors on the cellular hepatocytes in a warm-blooded host. These compounds form transport agents which are destined to transport a diagnostic or therapeutic cargo in liposomal form to a desired receptor site in the body of a warm-blooded animal, e.g., a human host. Accordingly, the metal complex, its dissociated form or combination of dissociated moieties which may function collectively or in tandem or a resulting general mixture thereof in the liposomal matrix comprises the transport agent which acts to selectively transport the designated cargo to the desired site-of-action.

A suitable lipid is selected from a group of lipids commonly employed to form liposomes. A suitable lipid or a mixture of lipids where lipid molecules function individually or in combination thereof is one which will dissolve the resultant metal complex and form a liposome which initially incorporates the metal complex therein. Typically, the selected lipid or mixture of lipids is maintained in suspension in aqueous media to form a liposomal carrier system.

Some suitable lipids include 1,2-distearoyl-sn-glycero-3-phosphocholine (DSL), 1,2-dipalmitoyl-sn-glycerol-3-phosphocholine (DPL), 1,2-dimyristoyl-sn-glycerol-3-phosphocholine (DML), cholesterol (CHOL), cholesterol oleate, dicetylphosphate (DCP), 1,2-distearoyl-sn-glycerol-3-phosphate, 1,2-dipalmitoyl-sn-glycero-3-phosphate, 1,2-dimyristoyl-sn-glycerol-3-phosphate, and a mixture of any of the foregoing lipids. A preferred lipid system is a mixture of DSL, CHOL and DCP which forms a charged liposomal structure.

Typically, the resultant metal complex is combined, then mixed and optionally reacted with the selected lipid or Liposome vehicle which is in a concentration sufficient to adequately dissolve and incorporate either all or a portion of the metal complex therein. The reaction is typically carried out at a temperature of 60° C. to 80° C. when 1,2-distearoyl-sn-glycerol-3-phosphocholine, a high transition temperature lipid, is employed. A time period from 30 minutes to 2 hours is generally required to completely dissolve and incorporate the metal complex and its accompanying dissociated molecular forms into the liposome matrix to form the transport agent or target delivery molecule. Lower temperatures may be used according to the transition temperature of the lipids selected for incorporation into the liposomal formation. Typically the selected metal compound, e.g. chromium chloride (III) hexahydrate, is first combined with the complexing agent in an aqueous buffered solution, e.g., 10 mM sodium acetate-activated buffer at pH 6.0, and allowed to equilibrate to pH 4.0 before the addition of the metal compound, e.g. chromium chloride (III) hexahydrate, and then the pH is adjusted between pH 3.2 and 3.3. Then the complexing agent is isolated and then combined with the liposomal constituent in a simple single-step addition procedure.

The loading of a therapeutic or diagnostic agent (pharmacological agent); begins when an aliquot of the resultant liposomal formulation and accompanying transport agent is introduced into an aqueous media or suspension along with a medicament or diagnostic agent to form a pharmacological delivery system or a liposomal delivery system. Typically, the pharmacological agent is encompassed by the liposomal matrix or entrapped in the liposomal core volume. For example, an aliquot of the liposomal formulation is introduced into a vial of Regular Human Insulin containing 100 International units of insulin/ml to formulate the insulin hepatocyte specific delivery system. The liposomal delivery system is a charged, e.g. negatively charged, carrier construct composed of the bridging agent metal complex or its dissociated form or a mixture thereof and the liposome, e.g. which optimally is composed of a mixture of 1,2-distearoyl-sn-glycero-3-phosphocholine, cholesterol and dicetyl phosphate, is then capable of delivering its designated cargo which, for example, is insulin, to the site of action in vivo, such as the hepatocytes in the liver of a warm-blooded host for the purpose of maintaining better glucose homeostasis in the liver and plasma.

Where a mixture of DSL, CHOL and DCP is employed, typically the hepatocyte targeting molecule or system comprises about 25.5 micro moles/ml of DSL, 6.85 micro moles/ml of CHOL and about 9.4 micro moles/ml with 0.465 micro moles/ml. of chromium complex.

A typical insulin derivative which is transported is one which is composed of a single or several combinations of monomeric insulin subunits ranging in composition from one monomeric subunit to nine associated monomeric subunits or a combination thereof, where at least one of the derivatives preferentially loads into the core or into the membrane or onto the surface of the liposome for delivery to the hepatocytes in the liver of a warm-blooded host. Additionally, this preferential loading is time dependent and increases over a period of five days when the temperature is maintained at 4° C.

The liposomal constructs of this invention provide useful agents for pharmaceutical application for administering an active agent to a host. Accordingly, the constructs of this invention are useful as pharmaceutical compositions in combination with pharmaceutically acceptable carriers. Administration of the constructs described herein can be via any of the accepted modes of administration for the biologically active substances that are desired to be administered. These methods include oral, parenteral, ocular, transdermal, nasal and other systemic or aerosol forms.

Depending on the intended mode of administration, the compositions used may be in the form of solid, semi-solid, or liquid dosage forms, such as, for example, tablets, suppositories, pills, capsules, powders, liquids, suspensions, or the like, preferably in unit dosage forms suitable for single administration of precise dosages. The pharmaceutical compositions will include the liposomal construct as described and a pharmaceutically acceptable excipient, and, optionally, may include other medicinal agents, pharmaceutical agents, carriers, adjuvants, etc.

A solution formulation can be placed into a spray device and be delivered as a spray. This type of drug delivery device is particularly well suited for application to large areas of skin, to highly sensitive skin or to the nasal or oral cavities.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as, for example, sodium acetate, sorbitan monolaurate, triethanolamine oleate, cyclodextrins, etc.

The amount of active compound administered will, of course, be dependent on the subject being treated, the type and severity of the affliction, the manner of administration and the judgement of the prescribing physician. In addition, if the dosage form is intended to give a sustained-release effect, the total dose given will be integrated over a total time period of the sustained-release device in order to compute the appropriate dose required. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 4.0% (w/v) of the total formulation. The drug component of the formulation will most likely be less than 20% (w/v) of the formulation and generally greater than 0.01% (w/v).

For oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like.

Typically, for oral administration, the compositions will take the form of a pill or tablet. Thus the composition will contain along with the active ingredient: a diluent such as lactose, sucrose, dicalcium phosphate, or the like; a lubricant such as magnesium stearate or the like; and a binder such as starch, gum acacia, gelatin, polyvinylpyrrolidone, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, etc. Actual methods of preparing such dosage forms are known, or will be apparent, to those skilled in this art; for example, see *Remington: The Science and Practice of Pharmacy*, 19th ed., 1995 (Mack Publishing Co., Easton, Pa.). The composition or formulation to be administered will, in any event, contain a quantity of the active compound in an amount sufficient to effectively treat the disorder or disease of the subject being treated.

Dosage forms or compositions containing active ingredient in the range of 0.005% to 5% with the balance made up from non-toxic carriers may be prepared. The exact composition of these formulations may vary widely depending on the particular properties of the drug in question. However, they will generally comprise from 0.01% to 5%, and preferably from 0.05% to 1% active ingredient for highly potent drugs, and from 2%-4% for moderately active drugs.

For a solid dosage form, the solution or suspension, in, for example, propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 5% in solution are employable, and will be higher if the composition is a solid which will be subsequently diluted to the above percentages. Preferably the composition will comprise 0.2-2% of the active agent in solution.

Nasal solutions of the liposomal construct alone or in combination with pharmaceutically acceptable excipients can also be administered.

Formulations of the liposomal construct may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

Leakage from prepared liposomes containing a therapeutic agent can be determined from conventional stability testing, both in a controlled storage environment approximating storage conditions, and in physiological fluid, depending on the intended mode of delivery of the liposomal construct.

Depending on the particular application, lipids can be produced and loaded by the methods disclosed herein, and those methods described in U.S. Pat. Nos. 4,946,787; 4,603,044; and 5,104,661, and the references cited therein. Typically, the aqueous liposomal formulations of this invention will comprise 0.1% to 10% active agent by weight (i.e., 100 mg drug per ml), and 1% to 4% lipid by weight in an aqueous solution, optionally containing salts and buffers, in a quantity to make 100% by volume. Particularly preferred are formulations which comprise 0.1% to 5% active agent. Most preferred is a formulation comprising 1% to 5% active agent by weight and up to 4% by weight of a lipid component in an amount of aqueous solution sufficient (q.s.) to make 100% by volume.

With respect to chromium, this hepatocyte targeting molecule complex was discovered by observing metal sequestration or chelation phenomena of a variety of metals and ligand structures in aqueous media. The metals that were investigated included chromium, calcium, iron, magnesium and manganese. These metals were evaluated for their reactivity with N-(2,6-diisopropylphenylcarbamoylmethyl) iminodiacetic acid. Surprisingly, while solutions were being stored over a period of a few days, a purple-to-violet-colored component was observed to precipitate from a solution of chromium chloride hexahydrate and N-(2,6-diisopropylphenylcarbamoylmethyl)iminodiacetic acid.

Chromium (Cr) is distinguished from the other metals in that it has an atomic number of 24 and a mass number of approximately 52 and belongs to the first series of transition elements. It resides in Subgroup VIB of the Periodic Table and is surrounded by three elements of known biological function. These include Vanadium (V), Manganese (Mn), and Molybdenum (Mo). Chromium is found in every oxidation state from −2 to +6 but only the ground state 0, +2, +3, and +6 are common oxidation states for chromium.

The nature of the chromium target molecule complex was discovered when Chromium (III) chloride was reacted with N-(2,6-diisopropylphenylcarbamoylmethyl) iminodiacetic acid. Specifically the N-(2,6-diisopropylphenylcarbamoylmethyl) iminodiacetic acid is present in aqueous media buffered by 10 mM sodium acetate-acetic acid buffer at pH 3.3.

The complex elicits a purple-to-violet color in keeping with its absorption spectrum in the visible range with a maximum absorption occurring at 5250 Å as shown in FIG. 1. Furthermore, the resultant complex is soluble in organic solvents, such as chloroform:methanol (2:1 v/v), but lacks any appreciable solubility in aqueous media.

The chromium target molecule complex substance was also discovered to be soluble in a mixture of lipids containing 1,2-distearoyl-sn-glycerol-3-phosphocholine, dicetyl phosphate and cholesterol. This finding led to the incorporation of the complex into a liposomal construct to form the transport agent. Later, after testing the complex in liposomal form using pancreatectomized mongrel dogs as an animal model, it was found that the resultant complex, is accompanied with the liposomal carrier, exhibits hepatocyte targeting specificity, i.e. is specific for cellulus hepatocytes, thereby allowing the construct to be targeted to the liver in a warm-blooded host.

Chromium Target Complex Preparation

The procedure below illustrates a chemical pathway for the preparation of a new organic hepatocyte targeting molecule which is organometallic in nature and lacks water solubility.

Procedure

Preparation of Stock A a. Weigh out 265 mg of N-(2,6-diisopropylphenylcarbamoylmethyl) iminodiacetic acid (Sigma) into a 100 ml round-bottom flask.

b. Add 50 ml of 10 mM sodium acetate buffer pH 6.0 and swirl to dissolve the constituents.

c. Sonicate the solution at 60° C. using a Tekmar Sonic Disrupter Model TM375 set at position #4 until the solution becomes evenly cloudy or clear. The pH of this solution should be between pH 2.7 and 3.0.

d. Add 0.1 N sodium hydroxide dropwise while mixing until the solution becomes water clear. The pH of this solution should be between pH 3.2 and 3.3.

Preparation of Stock B a. Weigh out 399 mg of chromium chloride hexahydrate ($CrCl_3.6H_2O$) (Sigma) into a 50 ml beaker.

b. Add 25 ml of 10 mM sodium acetate buffer pH 6.0 and mix until the $CrCl_3.6H_2O$ dissolves. The pH of this solution should be between pH 4.0 and 4.4.

Combine the Products of Stock A and Stock B a. Transfer the contents of Stock A to a 100 ml beaker and initiate slow stirring using a magnetic stirring bar.

b. Transfer the contents of Stock B into the mixing solution of Stock A. The pH of the solution should be between pH 3.2 and 3.3. Then cover the beaker with parafilm. This new solution is Complex C.

Synthesis a. Allow Complex C to sit at room temperature for at least three days. During this time period purple-to-violet-colored precipitate begins to form.

b. After the formation of a solid mass, filter off the liquid portion under vacuum through a small flitted glass filter.

c. Remove the solid from the filter and place them in a 50 ml round-bottom flask and dry on the Büchi Rotoevaporator at 60° C. under vacuum.

d. Store the dried solid in a clean dry vial at ambient temperature.

Preparation of Liposomal Formulation

The liposomal formulation used in the Dog Studies disclosed herein contains negatively charged liposomes and has the phospholipid composition shown in Table II below.

TABLE II

Liposomal Stock Constituents plus 0.2μ of previously dried $^{14}C$ cholesterol oleate

|  | DSL | CHOL | DCP | Chromium complex | |
|---|---|---|---|---|---|
| MW | 790.2 | 386.7 | 546.9 | 748.8 | |
| mg | 40.3 | 5.3 | 10.3 | .700 | =56.6 mg/2.0 ml or 28.3 mg/ml |
| μ moles | 51.0 | 13.7 | 18.8 | .93 | =84.4/2 ml |
| mole % | 60.4 | 16.2 | 22.3 | 1.1 | 100% |
| % by wt | 71.1 | 9.4 | 18.2 | 1.3 | 100% |

Sample Prepared in Deionized-Filtered Milli Q Water

The data in Table II illustrates that there are 60.4 molecules of 1,2-distearoyl-sn-glycero-3-phosphocholine (DSL):16.2 molecules of cholesterol (CHOL):22.3 molecules of dicetylphosphate (DCP):1.1 molecules of the chromium target molecule complex in the membrane of the liposomal formulation.

The liposomes are prepared by solubilizing the lipid constituents along with the chromium target molecule complex in a 25 ml round-bottom flask containing approximately 1.0 ml of chloroform:methanol (2:1 v/v). The mg amounts of the constituents are listed in Table II along with 0.2μ Ci of $^{14}C$ cholesterol oleate which was previously dried to a film in the round-bottom flask and used simply as a radiochemical tracer for following the lipid constituents.

The formulation containing the lipid constituents was evacuated using a Cole-Palmer Aspirator Pump Model #7049-00 and was turned slowly using a Büchi Rotoevaporator equipped with a water bath which was maintained at 62° C. After two hours of drying under vacuum at 62° C., 2.0 ml of 0.2μ filtered Milli Q water was added to the flask. The formulation was then hydrated for one hour at 62° C. while turning in a closed system. After completion of the hydration step, the formulation was sonicated under nitrogen for one minute in the round-bottom flask using a temperature controlled cuphorn transducer equilibrated at 62° C. and a Tekmar Sonic Disrupter Model #TM375 set at position #4.

Preparation of Hepatocyte Targeted Liposomal Formulation 3.0 ml of the resultant liposomal formulation was transferred to a 16 mm×112 mm polycarbonate test tube and sonicated under nitrogen for five more minutes using the Tekmar Sonic Disrupter set at position #4 while the temperature was maintained at 62° C. The formulation was then allowed to cool to room temperature before being sterile-filtered through a 0.2μ filter. The liposomal size was determined using a Coulter N4 Plus Particle Size Analyzer. Following filtration there was approximately 600-700 μl of formulation remaining. 400 μl of this formulation was added into a new 10.0 ml vial of Regular Human Insulin containing 100 International units of insulin/1.0 ml. After addition, the new product containing hepatocyte-directed insulin was stored and loaded with insulin at 4° C.

The addition of the 400 μl aliquot to the vial of insulin represents a 26-fold dilution of the original liposomal stock, whose constituents are delineated in Table I. The ratio of lipid to insulin in the vial of injectable insulin following aliquoting and liposomal dilution is 11,330 μg of lipid per 1000 units of insulin or 11.33 μg of lipid per one insulin unit. Another way of stating this relationship is that there are 11,330 μg of lipid per 38,500 μg of total insulin or 0.294 μg of lipid per μg of insulin or 3.40 μg of insulin per 1.0 μg of lipid in the vial of injectable insulin that has been prepared for subsequent administration.

Dog Dosing Experiment with Hepatocyte Targeted Liposomal Insulin

Figure 6:
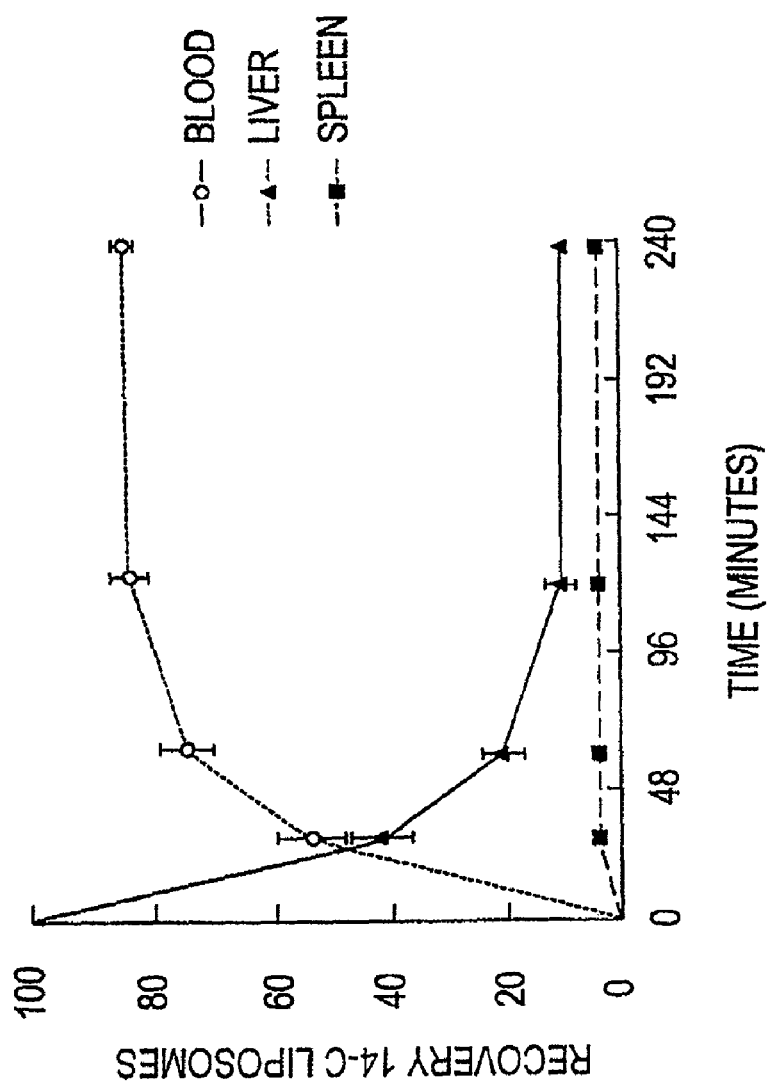
FIG. 6 shows the biodistribution of hepatic delivery vesicles (HDV) in various tissues of mice.

FIG. 6 illustrates data from a typical tissue distribution of hepatic delivery vesicles (HDV) of the resultant hepatocyte targeted liposomal formulation in normal mice that demonstrate the hepato-specificity which is important for the delivery of hormones such as insulin. After one hour, approximately 80% of the administered, radio-labeled HDV carriers were found in the liver.

Figure 7:
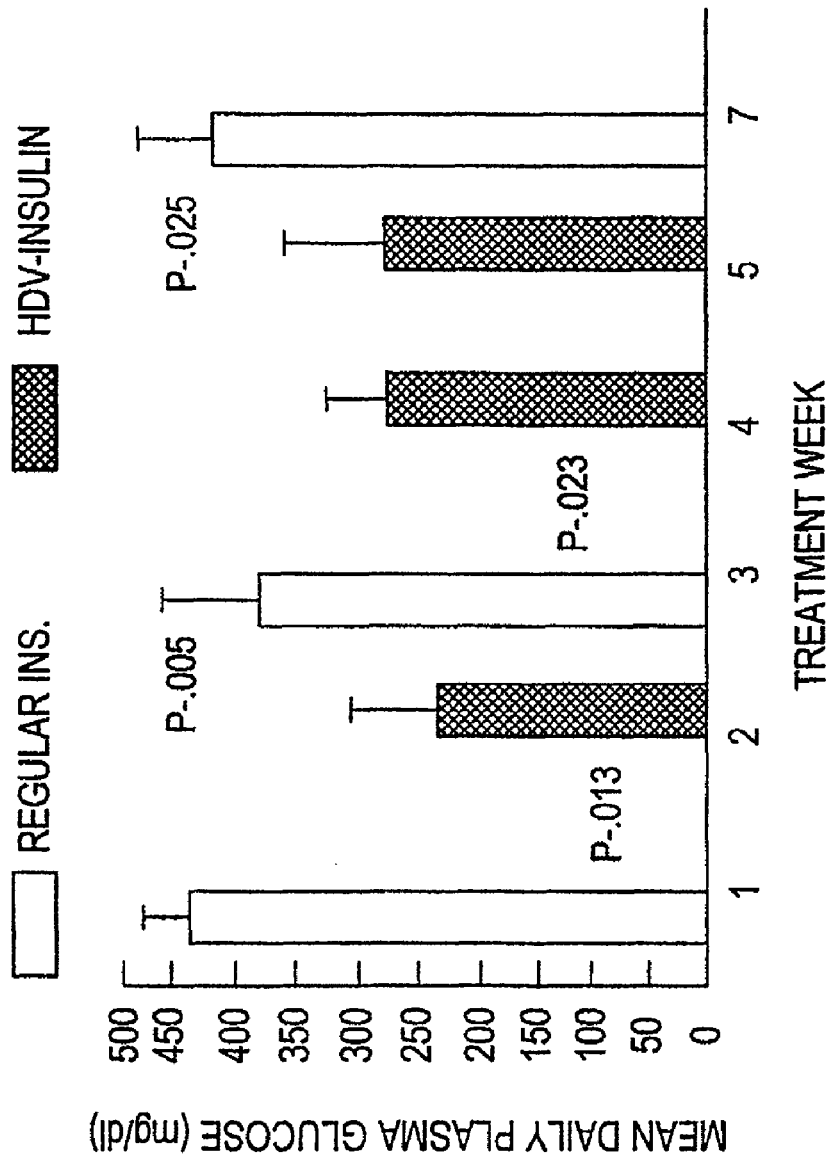
FIG. 7 illustrates the results produced in dogs receiving HDV-insulin treatment.

Insulin-dependent diabetes mellitus (IDDM) treatment is enhanced by adding HDV to commercially-available regular insulin. In a group of IDDM dogs (total pancreatectomy), the addition of HDV to Regular insulin resulted in markedly lowered daily mean plasma glucose values. The dogs were given standardized dog chow once daily at 9:30 AM and a snack at 3:00 PM. Insulin was given at 8:30 AM, 11:00 AM and 2:00 and, 6:00 PM. All five values were averaged to give a daily plasma glucose mean level. FIG. 7 summarizes these results. In this regard, FIG. 7 indicates that the HDV delivers approximately 1% of the regular insulin to the liver, activating the appropriate glucose storage mechanisms following the ingestion of a meal. It also inhibits hepatic glucose production during fasting.

Configuration of the Chromium Target Complex

Figure 2:
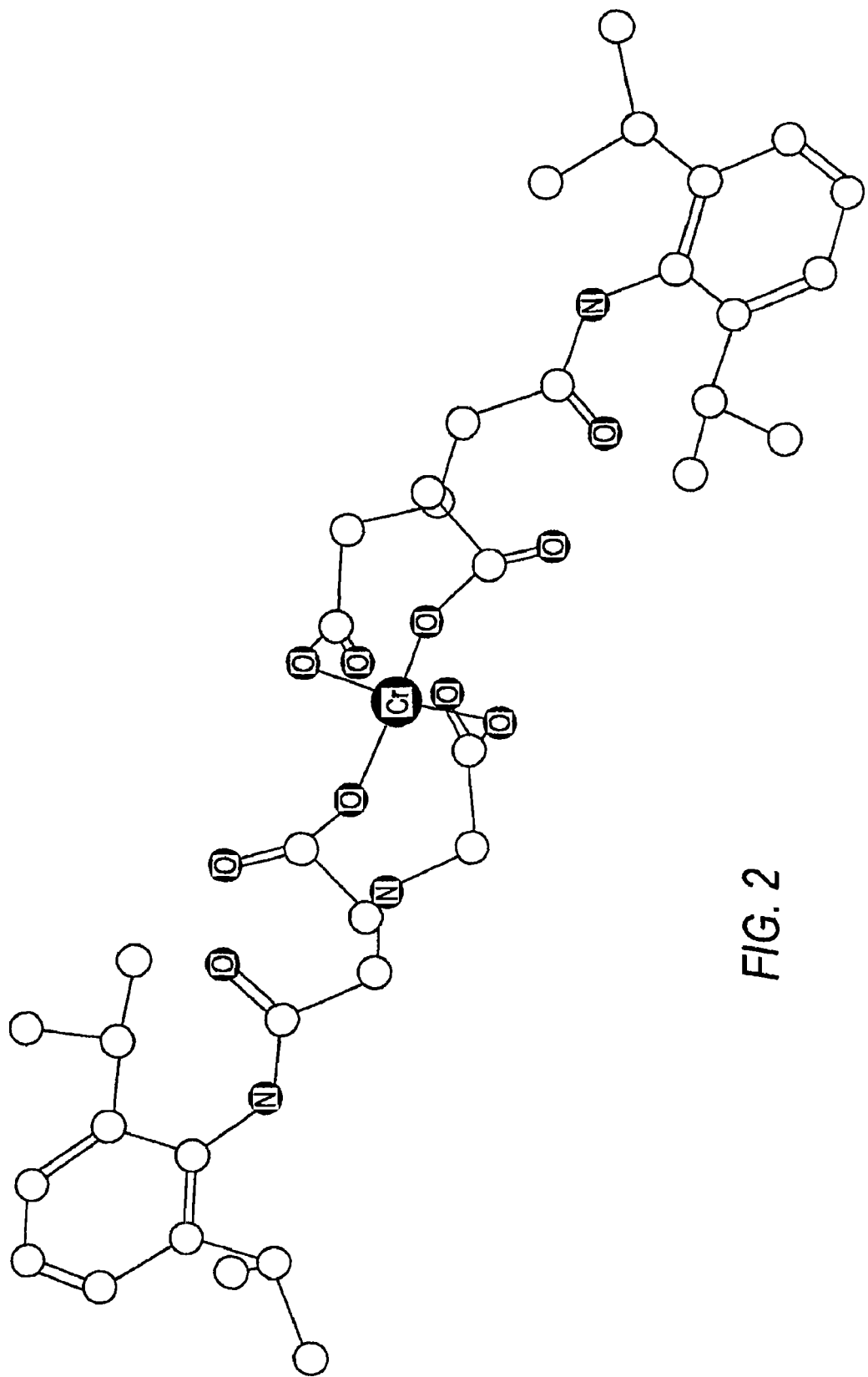
FIG. 2 is a ball and stick representation of the chromium target complex.
Figure 3:
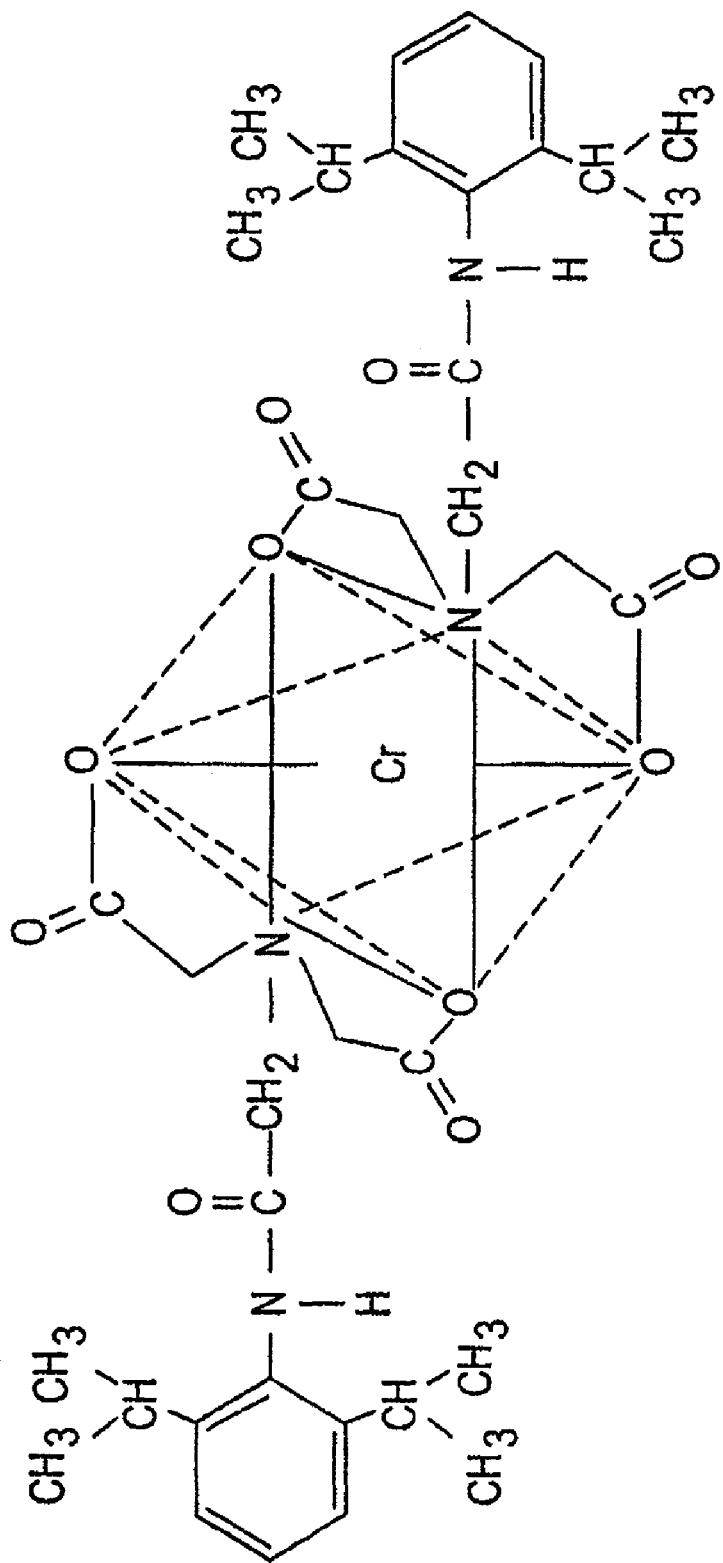
FIG. 3 illustrates a single chromium target complex.
Figure 4:
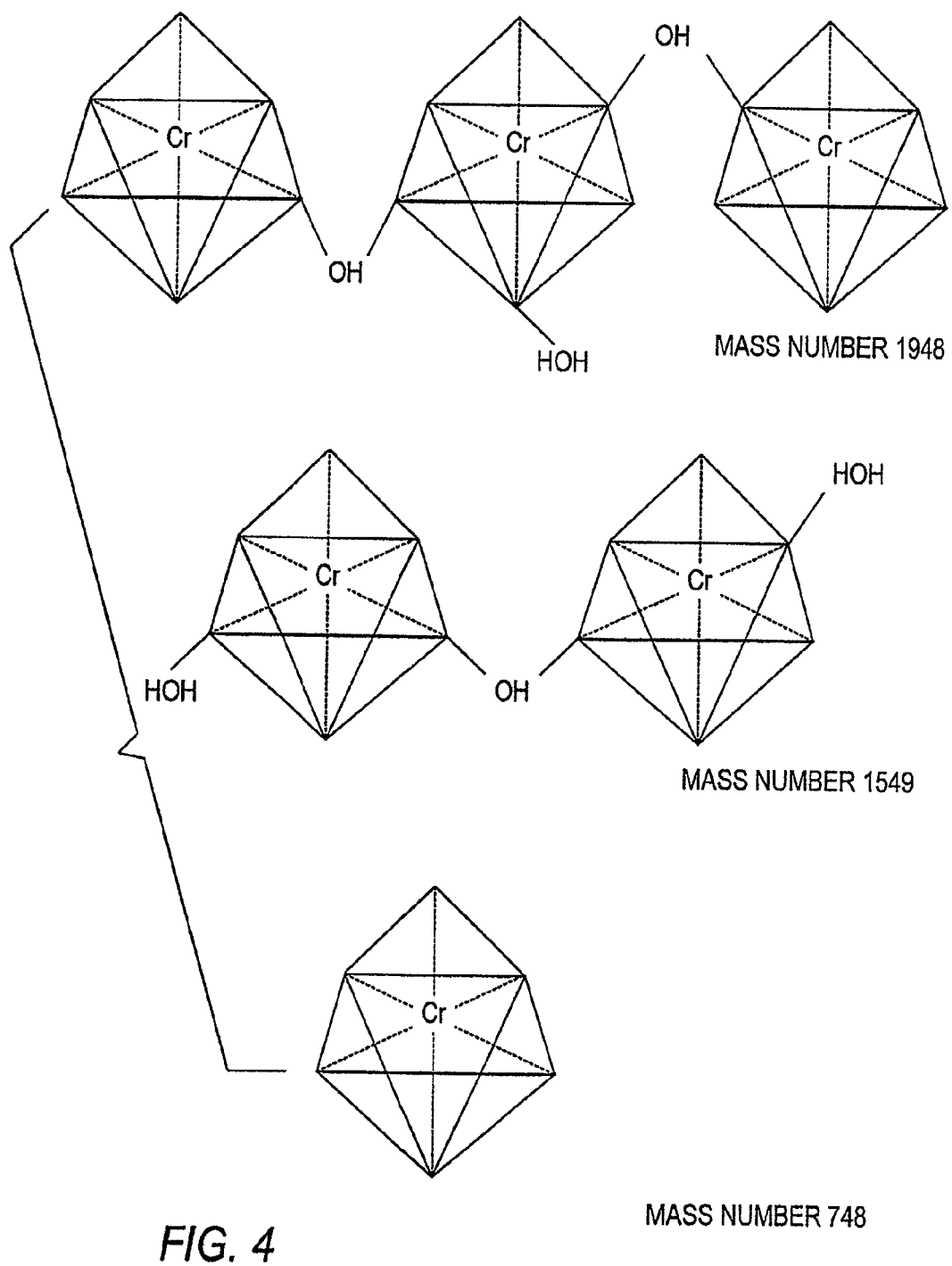
FIG. 4 shows various configurations of the chromium target complex.
Figure 5:
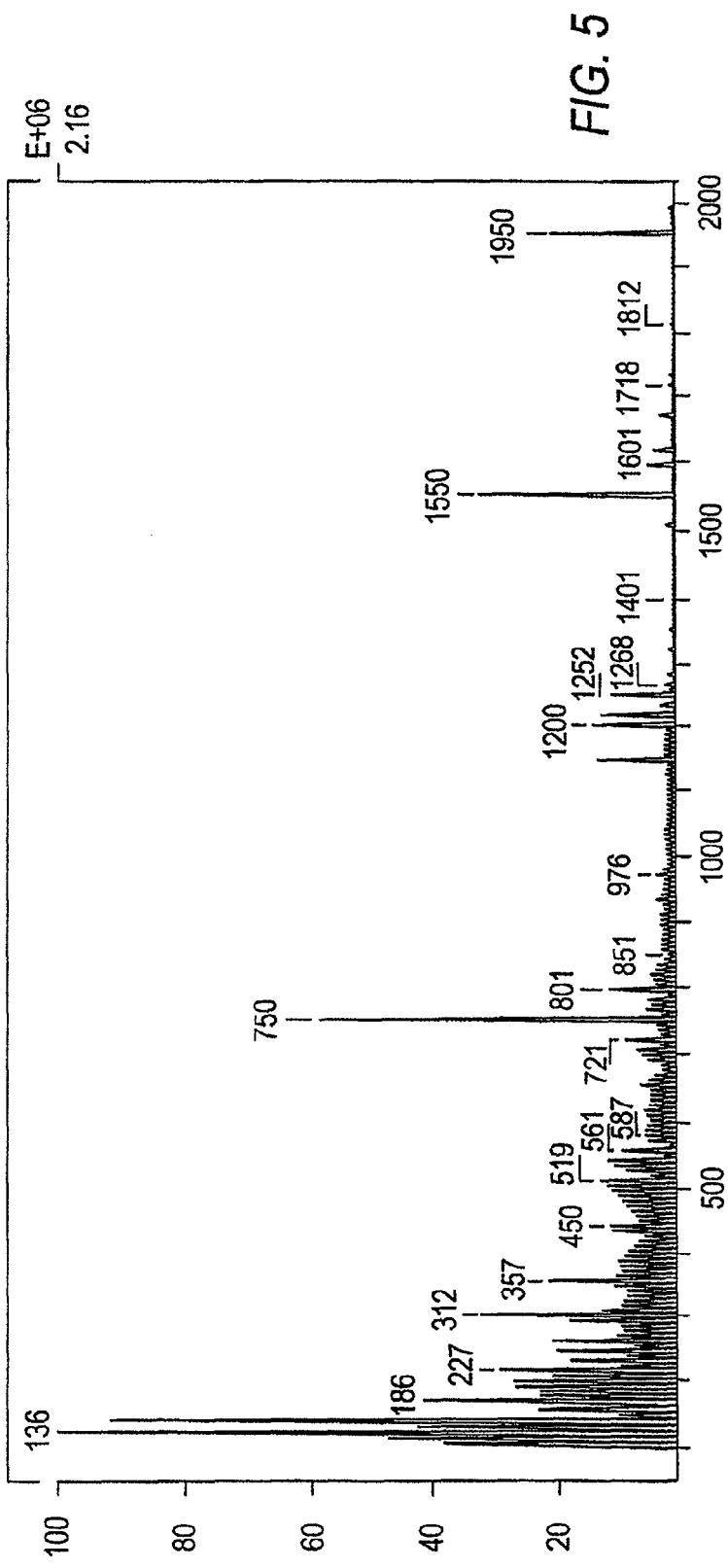
FIG. 5 is a printout of the results of mass spectroscopy analysis of the chromium target complex.

FIGS. 2 through 4 are ball and stick models of the chromium target molecule complex. In the structural formulas shown in FIG. 3, chromium has 6 ligands provided by four oxygen atoms and two nitrogen atoms. The configuration established around the chromium atom is most likely octahedral with chromium being at the center and the coordination sites with the various ligands being at the vertices of the octahedron. Simple multiples of this structure are shown in FIG. 4 and are supported by the data depicted in FIG. 5 generated by mass spectroscopy analysis.

FIG. 2 shows chromium with four ligands contributed by the four single bonded oxygens on the individual acetate functional groups. The nitrogen atoms do not play a role as ligand donors in this model. Since chromium has extra d orbitals into which electrons can be donated, the atom may acquire two hydroxyl groups and exhibit properties in concert with an oleated chromium structure. It is believed that this form or structure is less likely to be present in solution than the coordination complex employing the two nitrogen atoms as shown in FIG. 3. However, a portion of the oleated structure may be an intrinsic component of the chromium complex. The oleated structure is probably unstable when surrounded by a soluble phase since the exchange rate of donating ligands increases in an aqueous environment.

If the nitrogen atoms do not serve as donating ligands, then there is a reasonable probability that the chromium atom exhibits some degree of positive charge. Also, if the electrons from the hydroxyl groups fill the vacant orbitals of the chromium atom then the hydroxyl-chromium-hydroxyl complex probably exhibits some properties of oleated polynuclear complexes. In addition, this complex may have salt-like properties.

It is to be noted that $CrCl_3 \cdot 6H_2O$, which is the transition metal salt used in making the chromium target complex, manifests different properties than a simple alkaline earth salt, such as, $Na^+Cl^-$, which easily dissociates into separate ions when in solution. These differences arise because the electrons donated by some of the chlorine (Cl) groups in $CrCl_3 \cdot 6H_2O$ may be situated in the degenerate orbitals of chromium. Consequently, $CrCl_3$ may behave differently in aqueous media because the chlorines are more tightly bonded. This is a result of the coordinated ligands originating from the secondary valency of chromium.

The invention has been described with reference to the preferred embodiment. Obviously, modifications and alterations will occur to others upon reading and understanding of the preceding detailed description. It is intended that the invention be construed as including all such alterations and modifications insofar as they come within the scope of the appended claims or the equivalent thereof.

What is claimed is:

1. A method of producing a target delivery molecule, said process comprising:
   synthesizing a water insoluble target molecule complex comprising multiple linked individual units, wherein each of said multiple linked individual units comprises
      (a') a bridging component selected from the group consisting of a transition element, an inner transition element, a neighbor element of said transition element and a mixture of any of the foregoing elements; and
      (b') a complexing component comprising N-(2,6-diisopropylphenylcarbamoylmethyl)iminodiacetic acid;
         provided that, when said transition element is chromium, a chromium target molecule complex is formed; and
   combining said target molecule into a liposomal matrix to form the target delivery molecule.

2. The method of claim 1 wherein steps (a) and (b) are simultaneously carried out in situ.

3. The method of claim 1, wherein said liposomal matrix comprises a charged liposomal structure.

4. The method of claim 1, wherein said chromium target molecule complex is prepared by a method comprising
   combining an aqueous solution of N-(2,6-diisopropylphenylcarbamoylmethyl) iminodiacetic acid having an pH between 3.2 and 33 with an aqueous solution of a chromium compound having a pH between 4.0 and 4.4 to form a reaction solution;
   maintaining the reaction solution at a pH between 3.2 and 3.3 to form a complex solution; and,
   incubating said complex solution to form said chromium complex.

5. The method of claim 1, further comprising the step of combining a pharmacological agent with the target delivery molecule to form a pharmacological delivery system.

6. A method of producing a hepatocyte directed vesicle, said method comprising the steps of:
   reacting chromium with N-(2,6-diisopropylphenylcarbamoylmethyl)iminodiacetic acid to form a water insoluble chromium target molecule complex,
      wherein said complex comprises multiple linked individual units, wherein each of said multiple linked individual units comprises:
         a bridging component comprising chromium,
         and a complexing component comprising N-(2,6-diisopropylphenylcarbamoylmethyl)iminodiacetic acid; and
   adding the chromium target molecule complex to a liposome to form the hepatocyte directed vesicle.

* * * * *